United States Patent
Atkinson

(10) Patent No.: US 9,236,233 B2
(45) Date of Patent: Jan. 12, 2016

(54) COMBINATION ION GATE AND MODIFIER

(75) Inventor: Jonathan Richard Atkinson, Abbots Langley (GB)

(73) Assignee: Smiths Detection-Watford Limited, Watford, Hertfordshire (GB)

( * ) Notice: Subject to any disclaimer, the term of this patent is extended or adjusted under 35 U.S.C. 154(b) by 134 days.

(21) Appl. No.: 13/980,002

(22) PCT Filed: Jan. 20, 2012

(86) PCT No.: PCT/GB2012/000057
§ 371 (c)(1),
(2), (4) Date: Jul. 16, 2013

(87) PCT Pub. No.: WO2012/098364
PCT Pub. Date: Jul. 26, 2012

(65) Prior Publication Data
US 2013/0299712 A1   Nov. 14, 2013

(30) Foreign Application Priority Data
Jan. 21, 2011 (GB) .................................. 1101132.7

(51) Int. Cl.
*G01N 27/62* (2006.01)
*H01J 49/06* (2006.01)

(52) U.S. Cl.
CPC ............. *H01J 49/06* (2013.01); *G01N 27/622* (2013.01); *H01J 49/061* (2013.01)

(58) Field of Classification Search
CPC ................................ G01N 27/622; H01J 49/06
USPC ............................................... 250/389, 396 R
See application file for complete search history.

(56) References Cited

U.S. PATENT DOCUMENTS

| | | | |
|---|---|---|---|
| 5,227,628 A | 7/1993 | Turner | |
| 6,323,482 B1 * | 11/2001 | Clemmer | G01N 27/622 250/282 |
| 7,129,482 B2 * | 10/2006 | Miller | G01N 27/624 250/281 |
| 7,259,369 B2 | 8/2007 | Scott et al. | |
| 7,820,962 B2 | 10/2010 | Wynn et al. | |
| 7,932,489 B2 | 4/2011 | Atkinson et al. | |
| 7,994,475 B2 | 8/2011 | Atkinson et al. | |
| 7,999,224 B2 | 8/2011 | Atkinson | |
| 8,415,614 B2 | 4/2013 | Atkinson et al. | |
| 8,436,299 B2 | 5/2013 | Atkinson et al. | |
| 8,466,414 B2 | 6/2013 | Atkinson | |
| 8,766,173 B2 | 7/2014 | Atkinson | |
| 8,921,778 B2 | 12/2014 | Atkinson et al. | |
| 2007/0040111 A1 | 2/2007 | Scott et al. | |
| 2009/0039248 A1 | 2/2009 | Atkinson et al. | |
| 2010/0051800 A1 | 3/2010 | Atkiinson | |
| 2010/0127164 A1 | 5/2010 | Atkinson et al. | |

(Continued)

FOREIGN PATENT DOCUMENTS

| | | |
|---|---|---|
| CN | 2622705 Y | 6/2004 |
| CN | 101641593 A | 2/2010 |

(Continued)

*Primary Examiner* — David Porta
*Assistant Examiner* — Faye Boosalis
(74) *Attorney, Agent, or Firm* — Reinhart Boerner Van Deuren s.c.

(57) ABSTRACT

A detection device including an ionization region, an ion gate comprising two electrodes, an ion modifier comprising two electrodes, a drift chamber and a collector. The ion gate and ion modifier are combined so the ion gate is one of the ion modifier electrodes.

20 Claims, 2 Drawing Sheets

(56) References Cited

U.S. PATENT DOCUMENTS

| | | |
|---|---|---|
| 2010/0230588 A1 | 9/2010 | Atkinson et al. |
| 2011/0260053 A1 | 10/2011 | Atkinson et al. |
| 2011/0284739 A1 | 11/2011 | Atkinson et al. |
| 2011/0291000 A1 | 12/2011 | Atkinson et al. |
| 2011/0300638 A1 | 12/2011 | Atkinson |

FOREIGN PATENT DOCUMENTS

| | | |
|---|---|---|
| CN | 101647086 A | 2/2010 |
| EP | 1875222 | 1/2008 |

\* cited by examiner

COMBINATION ION GATE AND MODIFIER

CROSS-REFERENCE TO RELATED APPLICATION

This patent application is the national entry of International Patent Application No. PCT/GB2012/000057, filed on Jan. 20, 2012, also entitled "Combination Ion Gate and Modifier," which in turn claimed the benefit of Great Britain Patent Application No. 1101132.7, filed on Jan. 21, 2011, again entitled "Combination Ion Gate and Modifier," both of which are assigned to the assignee of the present invention and both of which are hereby incorporated herein by reference in their entirety.

BACKGROUND OF THE INVENTION

Field of the Invention

This disclosure relates to detection apparatus of the kind for detecting substances in a sample. The disclosure is more particularly, but not exclusively concerned with ion mobility spectrometers (IMS's).

Ion mobility spectrometers are used to detect the presence of chemicals in vapors or gases generally at atmospheric pressure. An IMS has some means to ionize the sample chemicals, such as a corona discharge or a radioactive source. A gate is opened to admit the molecular ion clusters into one end of a drift chamber across which a voltage is applied to cause the ion clusters to drift to the opposite end where they are collected on a collector plate. The molecular ion clusters might also include attached dopant ions. Dopant is introduced to aid in identifying ions of interest. The time taken for a molecular ion cluster to pass from the gate to the collector plate is dependent on the mass, size, shape and charge on the molecular ion cluster. By measuring this time an indication can be provided of the nature of the chemical.

In many cases it can be difficult to identify positively the substance of interest because the time of flight of the ion clusters produced may be very similar to that of ion clusters of different substances. Various arrangements have been proposed for improving the discrimination between different molecular ion clusters. One arrangement described in U.S. Pat. No. 6,797,943, to Karsten et al., which is hereby incorporated herein by reference in its entirety, involves fragmenting molecular ions using laser energy, a pyrolyzer or the like. The ion clusters are accumulated in a reservoir where they are exposed to the ion fragmentation energy prior to admittance to the drift chamber. One problem with this arrangement is that all the molecular ion clusters are subjected to fragmentation, which can lead to a large number of peaks on the spectrum, making analysis very difficult.

Although fragmentation can be useful, fragmentation may increase the overall energy used by IMS.

A dopant is selected to combine with one or more substances of interest so that identifiable spectral peaks are produced. A comparison of a spectrum from an undoped sample with the spectrum from the same sample doped may then show peaks in different positions and this could be used to help determine the analyte substance or substances of interest. A dopant also may be selected so that it does not combine with the interferent substance, or combines in a manner that produces a readily distinguishable output different from the substance of interest.

In U.S. Pat. No. 7,932,489 to Atkinson et al., which is hereby incorporated herein by reference in its entirety, an apparatus and method for modifying ions is disclosed. The apparatus includes means to apply a high electrical field to cause ion modification of the ions, such as fragmentation. The field may be a high strength RF field of around 2 MHz which is effective to cause ion modification of a significant percentage of the ions within the field. The strength of the field may be at least 10,000 V/cm and may be of the order of several tens of thousands of volts per centimeter. The RF field may be applied continuously or in bursts of the order of 18 in order to prevent corona discharge.

These fields enable sufficient energy to be transferred to the ions to cause ion modification. The modified or fragmented ions pass to the collector plate of the device with a different mobility from the unmodified ions and hence produce different peaks on the output spectrum. This can enable the apparatus to distinguish between two different ions having similar mobilities, since the modified versions of these ions will not generally have similar mobilities.

Ion modification can occur in both undoped and doped systems. In a doped system, two effects can occur. The ion modification process can remove the dopant adducts from ions without producing any modification of the ion itself. This may be because the dopant adduct is only removed from the ion when it has passed most of the way through the modifier and there is insufficient distance left in the modifier for further ion modification to take place. De-adducted ions may remain this way if the region of the ion modifier and beyond is free of dopant since, otherwise, recombination will occur. Ion modification of the ion itself can also occur if there is sufficient time left in the modifier region and energy available for it to do so.

SUMMARY OF THE INVENTION

According to the present disclosure, there is provided a detection device including an ionization region, an ion gate comprising two electrodes, an ion modifier comprising two electrodes, a drift chamber and a collector, characterized in that the ion gate and ion modifier are combined so the ion gate is one of the ion modifier electrodes.

In an embodiment, the ion gate comprises a fixed electrode and a moving electrode. These electrodes may be sets of parallel wires, wire meshes, or a combination of parallel wires and wire mesh.

The present disclosure also extends to a combined ion gate and ion modifier for use in a detection device, in which the ion gate comprises two electrodes through which current is passed to control the flow of ions into a detection apparatus, and in which the ion modifier comprises two electrodes through which a high frequency waveform is applied, characterized in that the ion gate forms one of the electrodes of the ion modifier.

In embodiments, the distance between the ion gate and the second electrode of the ion modifier is less than 1 mm, or less than 0.75 mm, for example it may be in the range 0.05 to 0.5 mm, or 0.1 to 0.4 mm, or 0.15 to 0.3 mm. The proximity of the second electrode of the ion modifier to the ion gate may be significant.

As a result of the proximity of the second electrode of the ion modifier to the ion gate, both the ion modifier electrode and the ion gate are activated substantially simultaneously, for example within 1 ms of each other.

The disclosure also extends to methods of detecting substances in a sample, in which the sample is supplied to an ionization region of a detection apparatus, the sample is ionized and is passed through a combined ion gate and ion modifier which both controls the flow of the sample to a drift chamber and fragments the ions within the sample, and the fragmented ions in the sample drift along the drift chamber to a collector.

As discussed above, the ion gate and ion modifier may be activated substantially simultaneously, for example within 1 ms of each other.

DESCRIPTION OF THE DRAWINGS

An embodiment of the device will now be described with reference to the following figures, in which.

DETAILED DESCRIPTION OF THE PREFERRED EMBODIMENT

Figure 1:
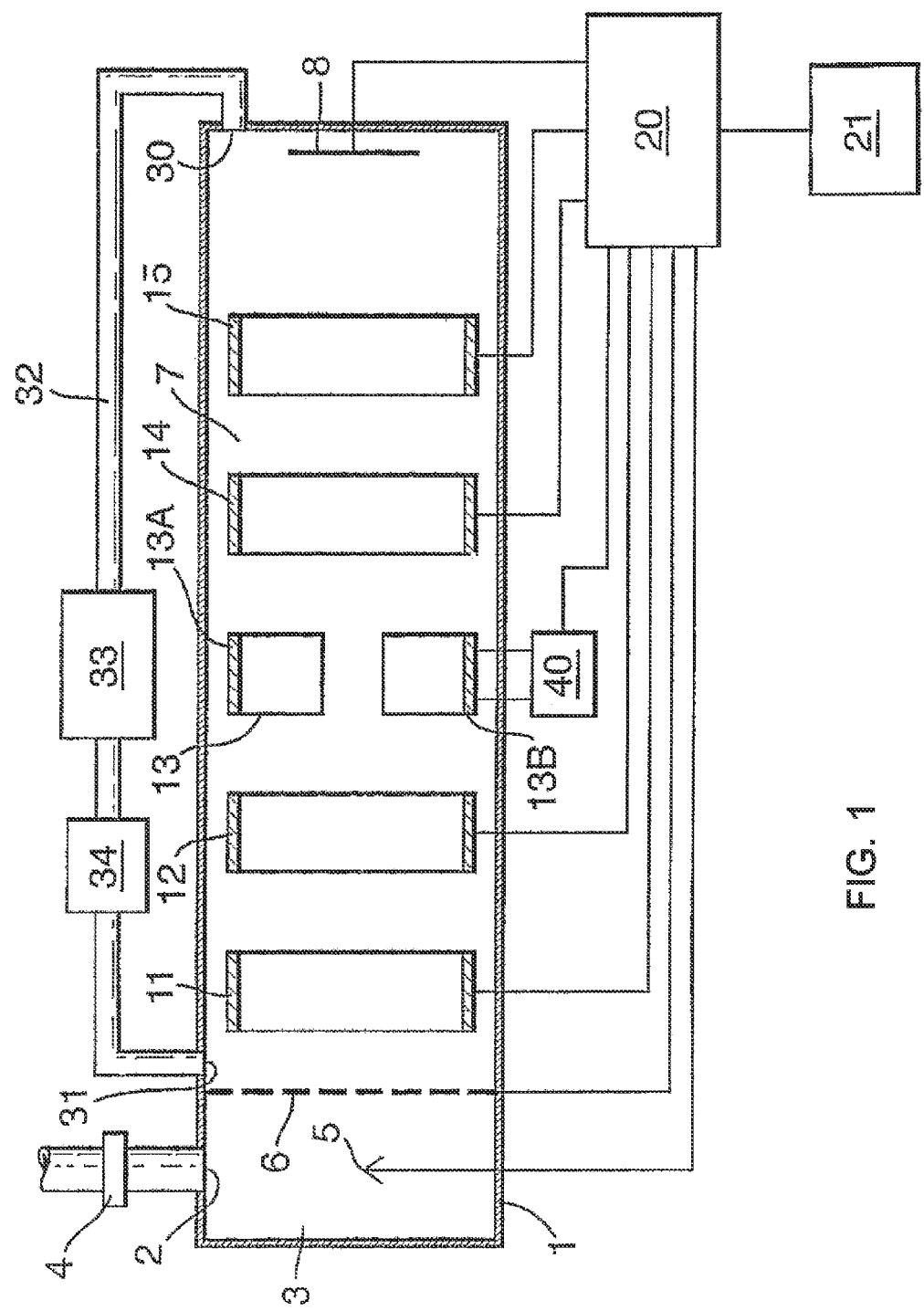
FIG. 1 shows, schematically, a system including a detector device.

Referring to FIG. 1, a detector device includes an elongate, tubular housing 1 the interior of which is substantially at atmospheric pressure. An inlet port 2 towards its left-hand end opens into an ionization region 3. A sample gas or vapor to be analyzed is supplied to the port 2 via a filter 4, in the conventional manner. The ionization region 3 includes a corona discharge point 5 or some other ionization means, such as a radioactive source, for ionizing the sample. An ion gate 6 separates the ionization region 3 from a drift chamber 1, which extends to the right-hand end of the housing 1 where an ion collector plate 8 is mounted. The drift chamber 7 includes a row of electrodes 11 to 15 spaced from one another along the length of the drift chamber 7.

The collector plate 8, electrodes 11 to 15, gate 6 and discharge point 5 are electrically connected to a processor control unit 20, which provides an output to a display or other utilization unit 21 representative of the substances detected.

Drift gas may be supplied to the right-hand end of the housing 1 at an inlet 30 to flow from right to left along the drift chamber 7, that is, in the opposite direction from the flow of ions. Drift gas is exhausted from the drift chamber 7 at its left-hand end through an outlet port 31. Gas flows between the outlet port 31 and the inlet 30 via a gas system 32, which includes a molecular sieve 33 and a pump 34. The sieve 33 may contain a dopant.

Ions produced in the ionization region 3 are admitted into the left-hand end of the drift chamber 7 when the gate 6 is opened. The ions drift from left to right along the drift chamber under the influence of the relatively low electrical field of about 250 V cm$^{-1}$ applied by the electrodes 11 to 15. The ions of different mobilities separate out from one another as they pass along the drift chamber 7 so that, at any one time, different ions will be in different regions of the drift chamber. The ions of different mobilities, therefore, reach the collector plate 8 at different times and produce output peaks to the processing unit 20 at different times.

A high electrical field to cause ion modification of the ions, such as fragmentation, may be applied in the drift chamber 7. The field is applied by means of the electrode 13, which includes two electrodes 13A and 13B spaced along the drift chamber's primary axis. In other embodiments, the two electrodes are spaced apart from one another across the diameter of the drift chamber 7. In still further embodiments, the ion modifier electrodes comprise two mesh structures, spaced from one another along the axis of the drift chamber.

Although in FIG. 1 these electrodes 13 A and 13B are shown midway along the drift chamber 7, they could be located at any point along the chamber, such as adjacent to the ionization region, or in the ionization region. These electrodes 13A and 13B are connected to a high voltage RF unit 40 controlled by the processing unit 20. The high voltage unit 40 is operable to apply a high strength RF field effective to cause ion modification of at least a portion of the ions within the field, e.g., a significant percentage of the ions within the field. The RF field may be applied continuously or in bursts. The field is typically a sinusoidal field applied between the two sets of wires arranged on opposite sides of the drift tube.

Figure 2:
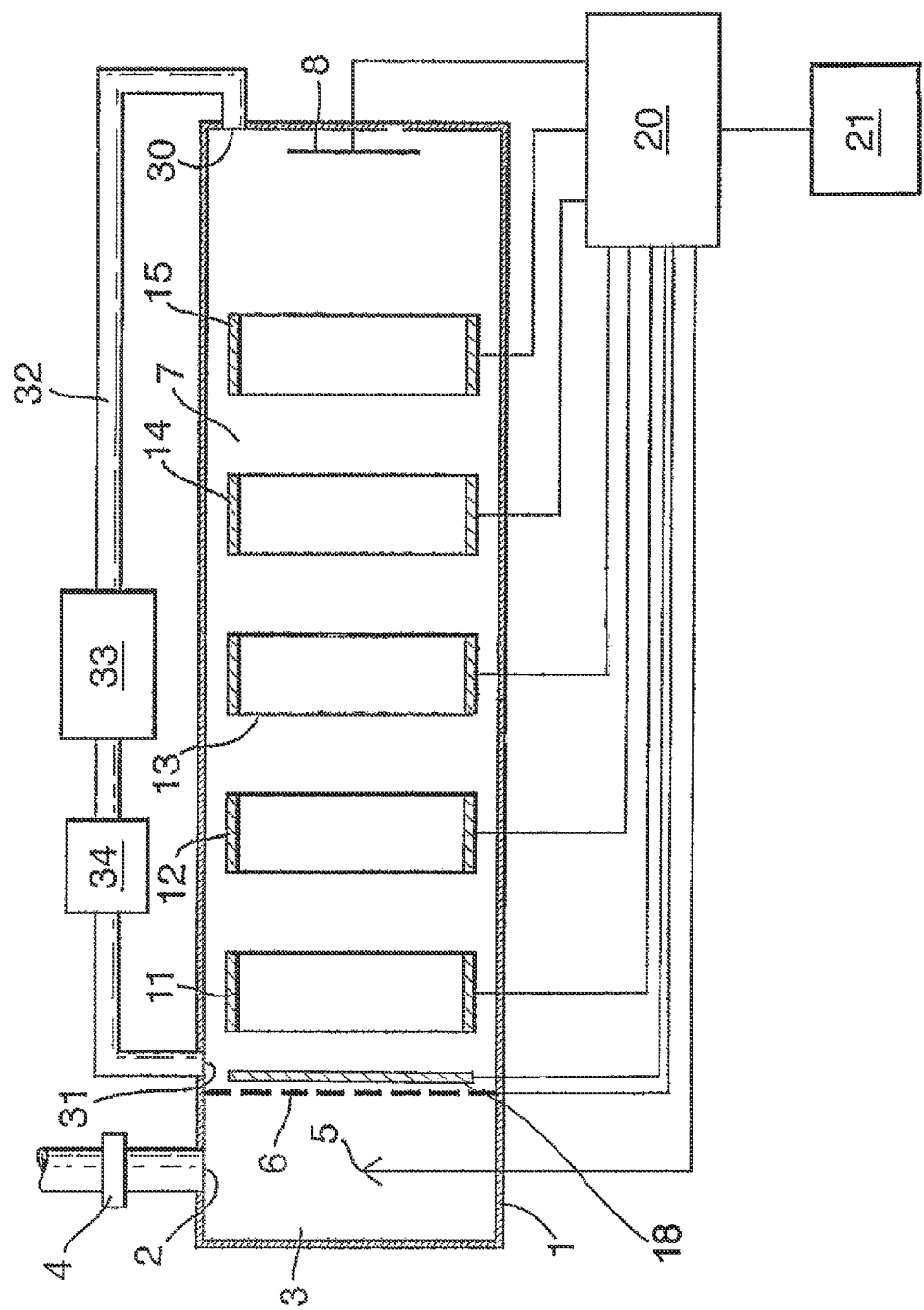
FIG. 2 shows, schematically, a detector device in accordance with the present disclosure.

Referring now to FIG. 2, the same reference numerals will be used here as in FIG. 1 for the same features. The ion modifier now comprises a single electrode 18 which is configured to operate in conjunction with the ion gate 6 which acts as the second electrode. The electrode 18 may be placed as closely as possible to the ion gate 6 and charged ions will, when the potential is correct on the gate, pass through the gate and be immediately modified or fragmented. For example, the electrode 18 may be placed as closely as possible to the ion gate 6 without resulting in arcing between the electrode and the ion gate.

In one embodiment, the ion modifier electrode 18 is positioned downstream of the ion gate. In another embodiment, the ion modifier electrode is positioned up stream of the ion gate.

The ion gate 6 is typically constructed of two sets of interdigitated parallel wires such as in a Bradbury Neilson shutter. Ions pass through the gate when the potentials on the two sets of wires are equalized, e.g., substantially equal. If they are offset then a field perpendicular to the direction of travel is established. Ions that strike the wires are not transmitted through the gate. One set of wires is typically at a fixed potential and the other may be moving.

The device of FIG. 2 has three electrodes to form the ion gate and the ion modifier. This reduction in the number of electrodes can increase the sensitivity of the device as fewer ions will be lost through collision with an electrode. Further, substantially all of the ions can be modified (when the ion modifier is activated) as the ion modifier is adjacent the ion gate. In the present embodiment, ion modification occurs upon entry into the drift chamber to increase the sensitivity of the device in comparison to a device that does not have the described configuration.

In operation and when the ion modifier is activated, one half of the sinusoidal waveform, e.g., substantially one half, is applied to electrode 18 and the other half to ion gate 6. It may be applied to just one of the electrodes of the ion gate 6 or it may be applied to both electrodes to prevent breakdown occurring between the fixed and moving grids of electrodes of the ion gate (for example a Bradbury Neilson shutter).

The greater sensitivity of the device will be realized in the generation of larger fragment ion peaks which will help identify with greater accuracy and certainty the identity of the sample. These peaks can be added to existing libraries of peaks to provide an end user with a more detailed definition of a particular sample.

The device would be arranged to operate without ion modification, i.e., the electrode 18 switched off. When an ambiguous substance is identified, the processing unit 20 can be configured to initiate ion modification in order to resolve the ambiguity. Alternatively, the device could be operated with the ion modification field on and then turn it off for short periods to confirm detection of a substance.

Having the ion modifier adjacent the ion gate minimizes or even avoids the problems with timing which occur with prior art systems. In the prior art (referring to FIG. 1), the ion modification field has to be initiated at a calculated predetermined time after opening the gate 6 such that those ions within a selected range of mobilities are the ion modification field electrodes 13 A and 13B when they are energized with the ion modification voltage. Such an operation helps to confine ion modification to selected ions only, thereby avoiding additional peaks being produced on the spectrum and facilitating identification.

However, the timing of the ion modification field may vary depending on the sample, such the size and speed of the ions, the drift gas, the relative location of the ion modifier compared to the ion gate, the applied electric fields, the presence of a dopant. The present invention minimizes or avoids the problem with timing by having the ion modification adjacent to the ion gate and having the ion gate as the second electrode in the modifier. The ion modifier electrode and the ion gate can be activated substantially simultaneously, for example within 1 ms of each other.

While the disclosure has been exemplified in the context of an IMS apparatus, the combined ion gate and ion modifier could also be used in any detection apparatus other than IMS apparatus.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

While the current application recites particular combinations of features in the claims appended hereto, various embodiments of the invention relate to any combination of any of the features described herein whether or not such combination is currently claimed, and any such combination of features may be claimed in this or future applications. Any of the features, elements, or components of any of the exemplary embodiments discussed above may be claimed alone or in combination with any of the features, elements, or components of any of the other embodiments discussed above.

What is claimed is:

1. A detection device comprising:
   an ionization region;
   an ion gate comprising two electrodes;
   an ion modifier comprising two electrodes;
   a drift chamber; and
   a collector;
   wherein the ion gate and ion modifier are combined whereby the ion gate comprises one of the ion modifier electrodes.

2. A detection device as defined in claim 1, wherein the ion gate comprises:
   a fixed electrode; and
   a moving electrode.

3. A detection device as defined in claim 2, wherein the fixed electrode and the moving electrode comprise sets of parallel wires.

4. A detection device as defined in claim 2, wherein the fixed and moving electrodes both comprise wire mesh.

5. A detection device as defined in claim 2, wherein the fixed electrode and the moving electrode comprise a combination of parallel wires and wire mesh.

6. A combined ion gate and ion modifier for use in a detection device, wherein the ion gate comprises:
   two electrodes to control the flow of ions into a detection apparatus by controlling the potential of the two electrodes; and
   wherein the ion modifier comprises:
   two electrodes through which a voltage waveform is applied;
   wherein the ion gate forms one of the electrodes of the ion modifier.

7. A combined ion gate and ion modifier as defined in claim 6, wherein the distance between the ion gate and a second electrode of the ion modifier is less than 1 mm.

8. A combined ion gate and ion modifier as defined in claim 7, wherein the distance between the ion gate and the second electrode of the ion modifier is less than 0.75 mm.

9. A combined ion gate and ion modifier as defined in claim 8, wherein the distance between the ion gate and the second electrode is in the range 0.05 mm to 0.5 mm, or 0.1 mm to 0.4 mm, or 0.15 mm to 0.3 mm.

10. A combined ion gate and ion modifier as defined in claim 6, wherein the second electrode of the ion modifier is configured to be activated substantially simultaneously with the ion gate.

11. A combined ion gate and ion modifier as defined in claim 10, wherein the second electrode is configured to be activated within 1 ms of the activation of the ion gate.

12. A combined ion gate and ion modifier as defined in claim 6, wherein the ion modifier electrode is positioned downstream of the ion gate with respect to the flow of ions.

13. A method as defined in claim 12, wherein the ion gate and ion modifier are activated substantially simultaneously.

14. A combined ion gate and ion modifier as defined in claim 6, wherein the ion modifier electrode is positioned upstream of the ion gate with respect to the flow of ions.

15. A method as defined in claim 14, wherein the ion modifier is activated within 1 ms of the activation of the ion gate.

16. A method of detecting substances in a sample, comprising:
   supplying the sample to an ionization region of a detection apparatus;
   ionizing the sample;
   passing the ionized sample through a combined ion gate and ion modifier; and
   operating the combined ion gate and ion modifier to both control the flow of the sample ions to a drift chamber and fragment the ions within the sample;
   wherein the fragmented ions in the sample drift along the drift chamber to a collector.

17. A method as defined in claim 16, wherein a high frequency waveform is applied to the ion modifier to modify the sample ions.

18. A method as defined in claim 16, wherein the combined ion gate comprises first and second electrodes.

19. A method as defined in claim 18, wherein the ion modifier comprises one of the first and second electrodes and a third electrode.

20. A method as defined in claim 18, additionally comprising:
moving one of the first and second electrodes with respect to the other of the first and second electrodes.

* * * * *